United States Patent
Zhao et al.

(10) Patent No.: US 8,439,498 B2
(45) Date of Patent: May 14, 2013

(54) TORIC INTRAOCULAR LENS WITH MODIFIED POWER CHARACTERISTICS

(75) Inventors: Huawei Zhao, Irvine, CA (US); Hendrik A. Weeber, Groningen (NL); Patricia Ann Piers, Groningen (NL)

(73) Assignee: Abbott Medical Optics Inc., Santa Ana, CA (US)

( * ) Notice: Subject to any disclaimer, the term of this patent is extended or adjusted under 35 U.S.C. 154(b) by 361 days.

(21) Appl. No.: 12/542,436

(22) Filed: Aug. 17, 2009

(65) Prior Publication Data

US 2009/0323020 A1    Dec. 31, 2009

Related U.S. Application Data

(63) Continuation-in-part of application No. 12/035,370, filed on Feb. 21, 2008, now Pat. No. 7,780,290.

(60) Provisional application No. 61/185,911, filed on Jun. 10, 2009.

(51) Int. Cl.
*G02C 7/00*    (2006.01)

(52) U.S. Cl.
USPC ............. 351/159.21; 351/159.01; 351/159.71

(58) Field of Classification Search .................. 351/159, 351/168–172, 176–177, 159.01–159.2, 159.21, 351/159.73–159.75, 159.71, 159.54, 159.38
See application file for complete search history.

(56) References Cited

U.S. PATENT DOCUMENTS

| | | | |
|---|---|---|---|
| 4,778,462 A | 10/1988 | Grendahl | |
| 4,795,462 A | 1/1989 | Grendahl | |
| 4,798,608 A | 1/1989 | Grendahl | |
| 4,798,609 A | 1/1989 | Grendahl | |
| 4,932,970 A | 6/1990 | Portney | |
| 5,016,977 A | 5/1991 | Baude et al. | |
| 5,066,301 A | 11/1991 | Wiley | |
| 5,652,638 A | 7/1997 | Roffman et al. | |
| 5,699,142 A | 12/1997 | Lee et al. | |
| 5,796,462 A | 8/1998 | Roffman et al. | |
| 6,142,625 A | 11/2000 | Sawano et al. | |
| 6,286,956 B1 * | 9/2001 | Oyama et al. | 351/159.41 |
| 6,457,826 B1 * | 10/2002 | Lett | 351/161 |

(Continued)

FOREIGN PATENT DOCUMENTS

| | | |
|---|---|---|
| EP | 0949529 A2 | 10/1999 |
| WO | 93/03409 | 2/1993 |
| WO | 03/009053 A1 | 1/2003 |

OTHER PUBLICATIONS

International Search Report for application No. PCT/US2010/038167, Mailed on Sep. 27, 2010, 2 pages.

*Primary Examiner* — James Greece

(74) *Attorney, Agent, or Firm* — Abbott Medical Optics Inc.

(57) ABSTRACT

An intraocular lens for correcting or reducing the astigmatism of a cornea includes an optical element that has optical properties and characteristics that make it tolerant of rotational misalignment, when compared to a comparable lens having a uniform astigmatism orientation across its entire optical element, leading to more relaxed tolerances for a surgeon that implants the lens. The optical element of the toric ophthalmic lens has meridians associated therewith, including a high power meridian and a low power meridian orthogonal to the high power meridian. The optical element has at least one radially modulated meridian along which power monotonically varies with increasing radial position.

20 Claims, 10 Drawing Sheets

U.S. PATENT DOCUMENTS

| | | |
|---|---|---|
| 6,491,721 B2 | 12/2002 | Freeman et al. |
| 6,533,416 B1 | 3/2003 | Fermigier et al. |
| 6,808,262 B2 | 10/2004 | Chapoy et al. |
| 6,923,539 B2 | 8/2005 | Simpson et al. |
| 6,923,540 B2 | 8/2005 | Ye et al. |
| 6,986,578 B2 | 1/2006 | Jones |
| 2002/0118337 A1 | 8/2002 | Perrott |
| 2004/0021824 A1 | 2/2004 | Ye et al. |
| 2004/0080710 A1* | 4/2004 | Wooley et al. ................ 351/159 |
| 2004/0150789 A1 | 8/2004 | Jones |

* cited by examiner

Amounts: same
Orientations:
$\theta - \Delta/2$
$\theta + \Delta/2$

Amounts: same

Orientations:
$\theta$
$\theta + \Delta/2$
$\theta - \Delta/2$

Amounts: same

Orientations:
$\theta - \Delta/2$
$\theta + \Delta/2$
$\theta - \Delta/2$
$\theta + \Delta/2$ Amounts: vary Orientations:
$\theta - \Delta/2$
$\theta + \Delta/2$
$\theta - \Delta/2$
$\theta + \Delta/2$ Amounts: vary Orientations:
vary

TORIC INTRAOCULAR LENS WITH MODIFIED POWER CHARACTERISTICS

RELATED APPLICATION

This application is a continuation-in-part application of, and claims priority to, U.S. patent application Ser. No. 12/035,370, filed Feb. 21, 2008, and to U.S. provisional application No. 61/185,911, filed on Jun. 1, 2009, the entire contents of each of which applications are hereby incorporated by reference in their entirety for all purposes as if fully set forth herein.

TECHNICAL FIELD

The subject matter described herein relates generally to an intraocular lens, and more specifically to an intraocular lens having variable power along its meridians.

BACKGROUND

There are many medical conditions that degrade the vision of a patient's eye. For instance, cataracts can cause the natural lens of an eye to become opaque. Fortunately, in many of these cases, the natural lens of the eye may be removed surgically and replaced with an intraocular lens, thereby restoring the vision of the eye.

Typically, the power required of the intraocular lens is determined by the properties of the patient's eye, which can include one or more refractive indices, curvatures, and/or distances. Any or all of these properties may be measured for a particular patient, so that a selected power for the intraocular lens matches the power required for a particular eye to within a particular tolerance, such as 0.25 diopters, 0.5 diopters, or 0.75 diopters, depending upon the patient's condition, the type of lens, and other factors.

In some cases, a particular cornea may have a rotational asymmetry that imparts astigmatism onto light that is transmitted through it. The astigmatism degrades the vision of the eye, and cannot be corrected by adjusting the power of the lens. In these cases, the intraocular lens may provide additional correction if it has a similar but opposite amount of astigmatism. Then, the astigmatism of the lens may cancel or reduce the astigmatism of the cornea, and the light reaching the retina of the eye may have reduced astigmatism and, therefore, may have improved vision. For example, an intraocular lens for an astigmatic patient might correct the astigmatism to within a tolerance of about 0.75 diopters.

In practice, there are difficulties with an equal-but-opposite astigmatism correction. In particular, there may be some residual astigmatism left in the eye, caused by, for example, a rotational misalignment between the astigmatic axis of the cornea and the astigmatic axis of the corrective intraocular lens. This rotational misalignment and its effects are shown in greater detail in the text that follows, and in FIGS. 1 and 2.

FIG. 1 is a schematic drawing of a lens pupil in the presence of astigmatism. Strictly speaking, this is astigmatism balanced by defocus so that RMS wavefront error is minimized. In terms of wavefront error, FIG. 1 has a given amount of astigmatism $W_{22}$ with an additional amount of defocus $W_{20}$ given by $W_{20}=-W_{22}/2$. In terms of Zernike polynomials, FIG. 1 has a given amount of astigmatism corresponding to the fifth and/or sixth Zernike polynomial terms, depending on the orientation of the astigmatism; in FIG. 1 the fourth Zernike term, corresponding to defocus, is zero.

The wavefront contour map 1 (labeled as "1") shows contours of equal phase in the pupil. In one direction, in this case the direction denoted by angle θ, the wavefront shows a negative curvature. In a direction perpendicular to that denoted by θ, the wavefront shows a positive curvature. At +/−45° degrees to θ, the wavefront is essentially flat.

For this document, the wavefront contour map 1 may be represented more simply by two equivalent schematic representations 2 and 3 (labeled as "2" and "3", respectively). Element 2 shows the pupil having a particular amount of astigmatism, denoted by +A, with an orientation denoted by θ. Note that the parallel lines in element 2 act as a guide for the viewer that show the orientation angle of the astigmatism, are not contours of equal phase. The "+" signs show regions of increasing phase in the pupil. Another representation, substantially equivalent to element 2, is element 3, in which an equal but opposite amount of astigmatism, denoted by −A, is oriented at 90° to that in element 2.

Using the drawing conventions of FIG. 1, FIG. 2 shows the effects of a rotational misalignment of a known lens that corrects for the astigmatism of a particular cornea. The circles in FIG. 2 represent the pupil area of the eye. The pupils are shown for simplicity as being circular, but they may include elongations or deformations. In general, the pupil areas correspond to physical locations on the anterior and/or posterior surfaces of the intraocular lens, so that the center of the pupil corresponds to the center of the lens surfaces, the edge of the pupil corresponds to the edge of the lens surfaces, and so forth.

The leftmost circle represents the astigmatism of the cornea of a particular patient's eye. The cornea astigmatism may have any particular orientation in the eye, and may deviate significantly from horizontal or vertical. In FIG. 1, the orientation of the cornea astigmatism is represented by an angle θ.

In practice, the magnitude of astigmatism is typically reported in power, usually in diopters. Alternatively, astigmatism may be reported as an axial separation between two foci, although this is seldom done for the optics of the eye. As a further alternative, astigmatism may be reported in terms of wavefront error. The power error, the axial separation and the wavefront error may all be related simply to each other, and all are substantially equivalent for the purposes of this discussion. In FIG. 2, the magnitude of the cornea astigmatism is denoted by an amount −A. The cornea, therefore, has an astigmatism that can be represented by its magnitude ("−A") and its orientation ("θ").

A known intraocular lens is shown schematically in the middle circle of FIG. 2. The lens itself has an equal and opposite amount of astigmatism as the cornea, which is denoted by the value +A. If this lens were to be implanted in the eye with its astigmatism precisely oriented to that of the cornea, then the corneal astigmatism would be completely or nearly completely cancelled. However, there is usually a small angular error in the orientation that arises during the implantation surgery, which is denoted in FIG. 2 as δ, so that the astigmatism of the lens is oriented at angle θ+δ after implantation. This angular error may be kept as small as possible, but may be limited in practice by the skill of the surgeon. While more skilled surgeons may be able to achieve a δ of about 5 degrees, less skilled surgeons may have difficulty meeting this value and may implant lenses with larger angular errors than 5 degrees.

Mathematically, it is found that the astigmatism of the cornea (amount −A, orientation θ), plus the astigmatism of the rotationally misaligned lens (amount +A, orientation θ+δ), results in a residual astigmatism with magnitude 2A sin δ, oriented at 45° to the angle (θ+δ/2). It is instructive to provide a numerical example of this 2A sin δ quantity, to illustrate the magnitudes of residual astigmatism that may result from angular misalignment of the lens.

Consider a cornea that has 2 diopters of astigmatism, and a lens that has 2 diopters (of the opposite sign) of astigmatism. If the lens is implanted with an angular error δ of 5 degrees, which is a rather tight tolerance for a surgeon, then the residual astigmatism is (2)(2 diopters)(sin 5°)=0.35 diopters. For a looser tolerance of 10 degrees, the residual astigmatism is (2)(2 diopters)(sin 10°)=0.7 diopters. A typical threshold for astigmatism is 0.25 diopters, so that if the light reaching the retina has less than 0.25 diopters of astigmatism, then the astigmatism does not significantly degrade the vision of the eye.

As a result, the residual astigmatism in the eye may impose a prohibitively tight tolerance on the angular orientation of the lens during implantation, resulting in a tedious and expensive implantation procedure. Accordingly, there exists a need for an intraocular lens having a reduced angular orientation tolerance.

BRIEF SUMMARY

A toric ophthalmic lens having an optical element is provided. The optical element has meridians associated therewith, including a high power meridian and a low power meridian orthogonal to the high power meridian. The optical element has at least one radially modulated meridian along which power monotonically varies with increasing radial position.

Another toric ophthalmic lens is also provided. The toric ophthalmic lens includes an optical element having meridians associated therewith, including a high power meridian and a low power meridian orthogonal to the high power meridian. The power varies with increasing radial position, and, along the high power meridian, between an originating position and a respective first radial position, power equals a respective nominal power. Moreover, between the respective first radial position and a respective second radial position, power is greater than the respective nominal power. Furthermore, between the respective second radial position and a respective third radial position, power is less than the respective nominal power.

Also provided is a method of manufacturing a toric ophthalmic lens having meridians associated therewith, including a reference meridian, a high power meridian, and a low power meridian orthogonal to the high power meridian. The method provides a standard toric lens function that defines power such that each meridian corresponds to a respective constant power. The method continues by applying a modification function to the standard toric lens function to obtain a modified toric lens function, wherein the modification function is a function of radial position and angle position relative to the reference meridian, and wherein the modified toric lens function results in non-constant power along at least one meridian. The toric ophthalmic lens is fabricated in accordance with the modified toric lens function.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Figure 3:
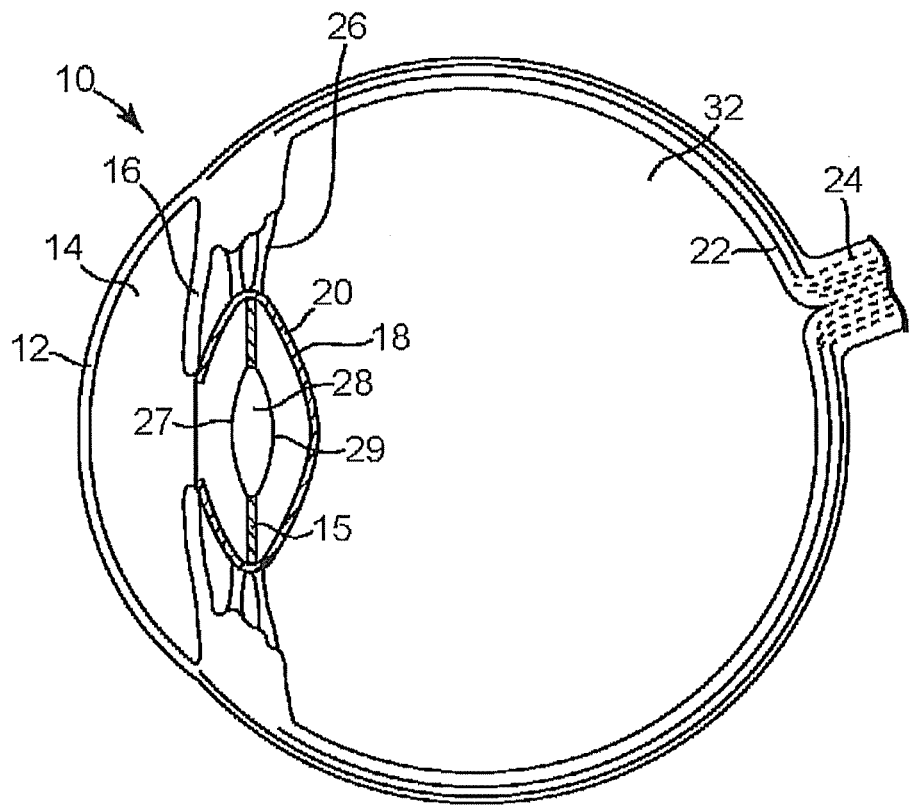
FIG. 3 is a schematic drawing of a human eye with an implanted intraocular lens.

FIG. 3 is a schematic drawing of a human eye 10, in which the natural lens of the eye has been removed and replaced with an intraocular lens. Light enters from the left of FIG. 1, and passes through the cornea 12, the anterior chamber 14, the iris 16, and enters the capsular bag 18. Prior to surgery, the natural lens occupies essentially the entire interior of the capsular bag 18. After surgery, the capsular bag 18 houses the intraocular lens, in addition to a fluid that occupies the remaining volume and equalizes the pressure in the eye. The intraocular lens is described in more detail below. After passing through the intraocular lens, light exits the posterior wall 20 of the capsular bag 18, passes through the posterior chamber 32, and strikes the retina 22, which detects the light and converts it to a signal transmitted through the optic nerve 24 to the brain.

The intraocular lens comprises an optic 28 and may include one or more haptics 15 that are attached to the optic 28 and may serve to center the optic 28 in the eye and/or couple the optic 28 to the capsular bag 18 and/or zonular fibers 26 of the eye.

The optic 28 has an anterior surface 27 and a posterior surface 29, each having a particular shape that contributes to the refractive properties of the lens. Either or both of these lens surfaces may optionally have a diffractive element made integral with or attached to the surfaces. The refractive and/or diffractive elements on the anterior and/or posterior surfaces may have anamorphic or toric features that can generate astigmatism. Typically, this astigmatism may be used to offset the astigmatism from a particular cornea in an eye.

The cornea astigmatism magnitude and orientation may be measured by topographic measurements, surface profilometry or by reflected or transmitted wavefront measurements (e.g., using a Hartmann-Shack wavefront sensor, or the like). Once the astigmatism magnitude is determined, a lens may be selected or fabricated to reduce or at least partially cancel the corneal astigmatism. For example, a practitioner may select an intraocular lens from a kit of lenses, with each lens in the kit having a discrete value of astigmatism. The astigmatism values in the kit may be in increments of 0.25 diopters, 0.125 diopters, or any suitable value. Alternatively, the intraocular lens may be custom-designed and fabricated to offset the cornea astigmatism of a particular patient.

The intraocular lens has a pupil or aperture. For the purposes of the present disclosure, the pupil of an intraocular lens means the opening of a lens or optic that restricts the extent of a bundle of light rays from a distant source that can imaged or focused by the lens or optic. The lens pupil is usually circular and is specified by its diameter. Thus, the lens pupil represents the full extent of the lens or optic usable for forming the conjugate image of an object or for focusing light from a distant point source to a single focus or to a plurality of predetermined foci, in the case of a multifocal optic or lens. In some embodiments, the lens pupil has the same or substantially the same diameter as the optic. Alternatively, the diameter of the lens pupil may be smaller than the diameter of the optic, for example, due to the presence of a glare or PCO reducing structure disposed about a peripheral region of the optic. Many of the figures in this document show an exemplary pupil, when viewed from a position along the optical axis of the lens.

Figure 4:
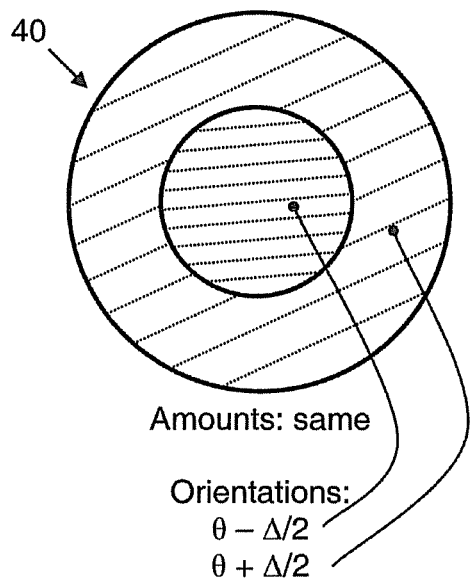
FIG. 4 is a schematic drawing of a pupil of an intraocular lens with two concentric zones, each zone having a different astigmatism orientation.

FIG. 4 is a schematic drawing of the pupil 40 of an embodiment of an intraocular lens. The pupil 40 is segmented into two concentric, radial zones. Each zone may include the same amount of astigmatism (denoted as amount "A") but with orientations that differ by an angle $\Delta$. For example, if a nominal or average orientation of the astigmatism in the all the zones is at an angle $\theta$, the orientations of the astigmatisms of the zones may be at "$\theta - \Delta/2$" and "$\theta + \Delta/2$".

The amount of astigmatism in each zone may be matched to the astigmatism of the cornea of the eye in which the lens is to be implanted. For instance, if the cornea has −2 diopters of astigmatism, then lens 30 may have +2 diopters of astigmatism in each zone. Alternatively, the zones may have powers that differ from that of the cornea and/or that differ from one another. In some embodiments, the lens 30 is part of a catalog or kit that includes lenses having discrete values of astigmatism, where a surgeon or practitioner chooses the amount of lens astigmatism that is closest to the equal and opposite value of the cornea astigmatism.

The astigmatisms in the two zones have orientations that differ by angle $\Delta$. When the lens is perfectly aligned with a cornea astigmatism having orientation $\theta$, the two zones have astigmatism orientations of $\theta - \Delta/2$ and $\theta + \Delta/2$. In practice, there may be a particular tolerance on the angular error of the lens that occurs during implantation, such as +/−5°, +/−10°, and so forth, with smaller tolerance numbers being harder for a surgeon to achieve. The angular separation of the orientations $\Delta$ may be related to the implantation angular tolerance $\delta$, and may take on values of $\delta/4$, $\delta/3$, $\delta/2$, $\delta$, $2\delta$, $3\delta$, $4\delta$, and so forth. For instance, if the lens is specified to be implanted to within +/−5°, then the angular separation of the astigmatism orientations $\Delta$ may be 2.5°, 5° or 10°.

Figure 2:
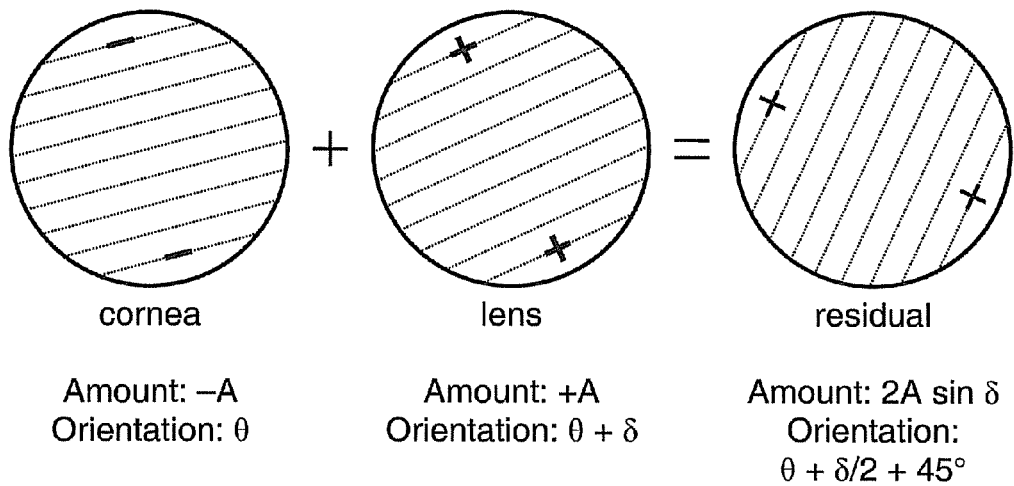
FIG. 2 is a schematic drawing of the residual astigmatism resulting from an astigmatic cornea and a known, rotationally misaligned, astigmatic lens.
Figure 5:
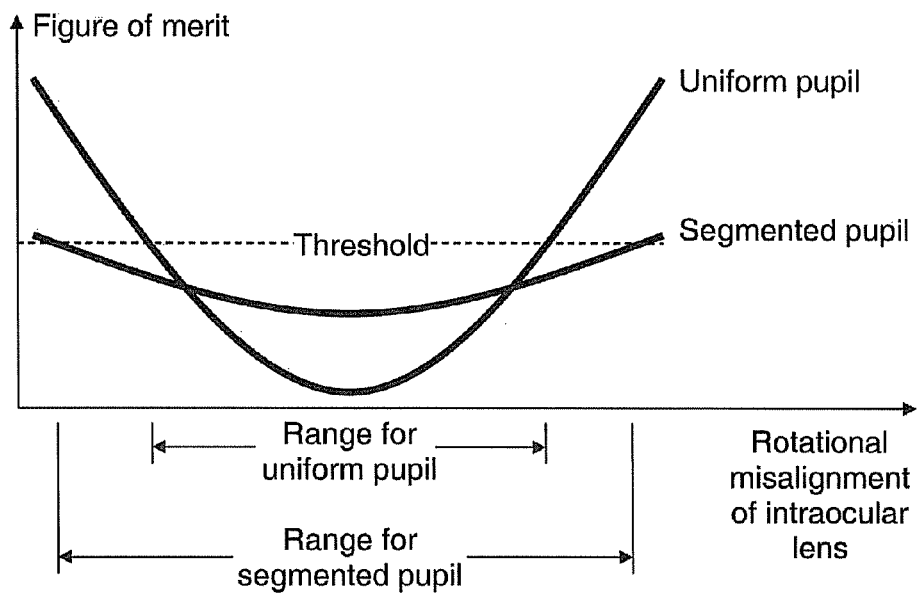
FIG. 5 is an exemplary plot of the relative performance of the lenses of FIGS. 2 and 4, as a function of rotational misalignment.

The benefits of such a segmented pupil may be seen in the plots of FIG. 5, which is a plot of performance versus rotational misalignment, for lenses having uniform pupils, such as the known lens of FIG. 2, and having segmented pupils, such as the lens of FIG. 4.

In FIG. 5, the horizontal axis is rotational misalignment, with minima for both curves occurring where the astigmatism of the intraocular lens is rotationally matched to the astigmatism of the cornea. The uniform pupil may have a better "optimal" value than the segmented pupil, but the slope away from this "optimal" value is generally larger for the uniform pupil. The figure of merit value may increase more slowly for the segmented pupil than for the uniform pupil, and may cross a particular threshold value at a larger rotational misalignment value than the uniform pupil. As a result, the segmented pupil may have a larger (or more loose) tolerance on rotational misalignment, which can ease the cost and/or difficulty of implantation.

The vertical axis is figure of merit, which may be any suitable figure of merit used in vision or optics measurements. For instance, figures of merit that increase away from an optimal (minimum) value include RMS spot size, RMS wavefront error, Zernike polynomial values, wavefront error terms, point spread function dimension(s), or any other suitable figure of merit. Other figures of merit may decrease away from an optimal (maximum) value, which is the opposite of the exemplary plot of FIG. 5. One such figure of merit is linear Modulation Transfer Function (MTF) along a particular direction, at a particular spatial frequency, such as 25, 50, or 100 lines pairs per mm. Another figure of merit is rotational MTF at a particular rotational frequency, such as 30 circles per degree. Another figure of merit that decreases from an optimal maximum value may include Strehl Ratio.

Because the overall shape of the lens pupil in FIG. 4 is rotationally symmetric, it is possible to calculate analytically an RMS wavefront error that arises from rotational misalignment of an intraocular lens having such a pupil. The following paragraphs provide a non-limiting example of such a calculation.

Beginning with an expression for the wavefront aberration W as a function of normalized pupil coordinates $\rho$ and $\theta$, keeping only the terms corresponding to defocus and astigmatism oriented in direction $\theta_0$:

$$W(\rho,\theta) = W_{20}\rho^2 + W_{22}\rho^2 \cos^2(\theta - \theta_0)$$

Figure 1:
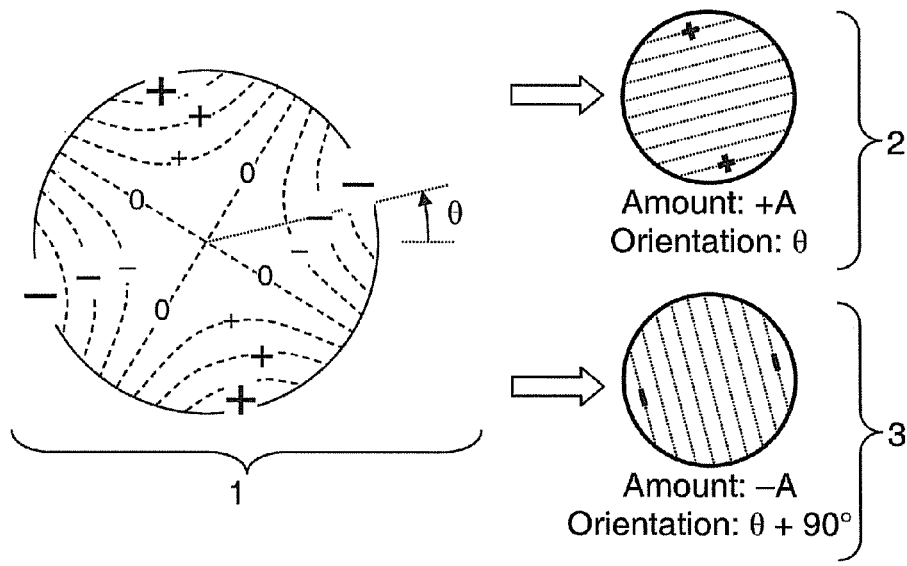
FIG. 1 is a schematic drawing of a lens pupil in the presence of astigmatism.

Assume that that the value of defocus $W_{20}$ is $-W_{22}/2$, so that the pupil wavefront appears as shown in FIG. 1. Rewrite the wavefront W as:

$$W(\rho, \theta) = W_{22}\rho^2 \frac{\cos[2(\theta - \theta_0)]}{2}$$

Calculate the wavefront variance, $\sigma_W^2$ for the wavefront $W(\rho, \theta)$ above:

$$\sigma_W^2 \equiv \langle W^2 \rangle - \langle W \rangle$$

$$= \frac{1}{\pi}\int_0^{2\pi}\int_0^1 W^2 \rho\, d\rho\, d\theta - \frac{1}{\pi}\int_0^{2\pi}\int_0^1 W \rho\, d\rho\, d\theta$$

$$= \frac{1}{4}\int_0^1 W_{22}^2 \rho^5\, d\rho$$

The RMS wavefront error is the square root of the wavefront variance, given above.

Assume that the astigmatism $W_{22}$ is constant within each zone and is equal to $2A \sin(\delta - \delta_i)$ within each zone i. Each zone has astigmatism oriented at $\delta_i$ and is bounded by outer radius $\rho_i$ and inner radius $\rho_{i-1}$, and $\delta$ is the rotational misalignment of the intraocular lens. The wavefront variance becomes:

$$\sigma_W^2 = \frac{A^2}{24}\begin{bmatrix}(2-2\cos[2(\delta-\delta_1)])(\rho_1^6 - 0^6) + \\ (2-2\cos[2(\delta-\delta_2)])(\rho_2^6 - \rho_1^6) + \ldots + \\ (2-2\cos[2(\delta-\delta_i)])(\rho_i^6 - \rho_{i-1}^6) + \ldots + \\ (2-2\cos[2(\delta-\delta_n)])(1^6 - \rho_{n-1}^6)\end{bmatrix}$$

Consider the special case of two concentric zones. A first zone extends from the center of the pupil at $\rho=0$ to a radius of $\rho=\rho_0$, with an astigmatism of magnitude A and orientation $+\Delta/2$. A second zone extends from the radius of $\rho=\rho_0$ to the edge of the pupil at $\rho=1$, with an astigmatism of magnitude A and orientation $-\Delta/2$. The wavefront variance, $\sigma_W^2$, simplifies to:

$$\sigma_W^2 = \frac{A^2}{24}[2 - 2(\cos 2\delta \cos\Delta - [1 - 2\rho_0^6]\sin 2\delta \sin\Delta)]$$

As a check, this reduces to a single zone if $\rho_0=0$ or 1, with the expected result of:

$$\sigma_W^2 = \frac{A^2}{24}\left[4\sin^2\left(\delta \pm \frac{\Delta}{2}\right)\right]$$

The preceding calculation applies when RMS wavefront error is used as the specific figure of merit. Other figures of merit may be used as well, including any or all of those listed above, although the algebra for these other figures of merit may be more cumbersome than for RMS wavefront error.

An advantage of the segmentation scheme of FIG. 4, in which the lens pupil is segmented into concentric portions, with each portion having the same amount of astigmatism but different orientations for each astigmatism axis, is that the resulting lens becomes less sensitive to rotational misalignment, during and/or after implantation. The peak performance of the segmented lens may be less than that of the uniform lens when each lens is optimally aligned; however, the performance of the segmented lens, as a function of rotational misalignment, may deteriorate more slowly than for the uniform lens. For example, as the performance of one segment decreases with rotational misalignment, the performance of the other may increase, wherein the performance of one segment partially offsets the other, thus decreasing sensitivity to rotational misalignment.

In FIG. 4, the pupil 40 is divided so that the central zone has a radius equal to roughly half the pupil radius, and an angular separation between astigmatism axes of $\Delta$. When optimally aligned to a cornea with astigmatism $\theta$, the two zones have astigmatism orientations of $\theta+/-\Delta/2$. The alignment tolerance 6 on the lens may be on the order of $\Delta$, with $\delta$ being equal to $\Delta$ or being equal to $\Delta/4$, $\Delta/3$, $\Delta/2$, $2\Delta$, $3\Delta$, $4\Delta$, or any suitable multiplicative factor times $\Delta$. In other embodiments, the pupil 40 is divided so that the central zone has an area that is equal to roughly half the pupil area. Other radius or area ratios between the zones are anticipated in accordance with the particular requirements of a situation or design.

In addition to the geometry of FIG. 4, there are other possible geometries, shown in FIGS. 6-14, and described in a non-limiting way in the text that follows. In the pupil 60 of FIG. 6, the central zone may have a radius greater than half the radius of the full pupil. The astigmatism amounts are the same in each zone, and the astigmatism orientations are angularly separated by $\Delta$. Although not shown in the figures, the central zone may also have a radius less than half the radius of the full pupil.

Figure 7:
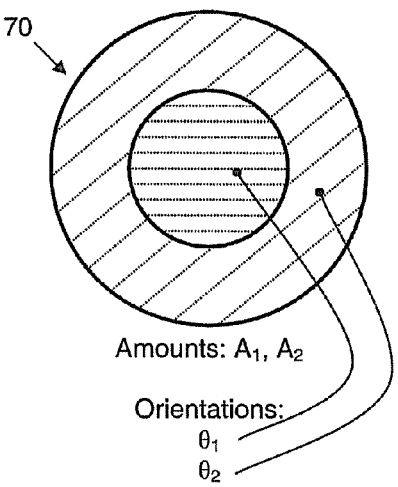
FIG. 7 is a schematic drawing of a pupil of an intraocular lens with two concentric zones, in which each zone has both a different astigmatism amount and a different astigmatism orientation.

In the pupil 70 of FIG. 7, the astigmatism amounts may be different in the central and outer zones.

Figure 6:
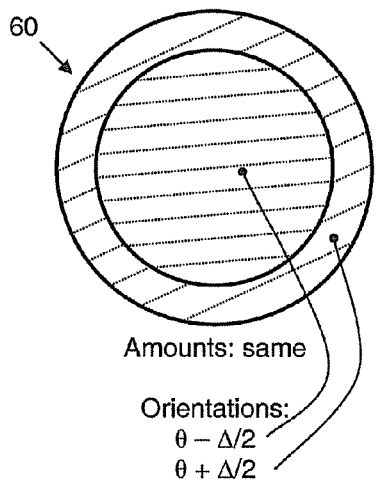
FIG. 6 is a schematic drawing of a pupil of an intraocular lens with two concentric zones, in which the central zone has a radius different than half the radius of the full pupil.
Figure 8:
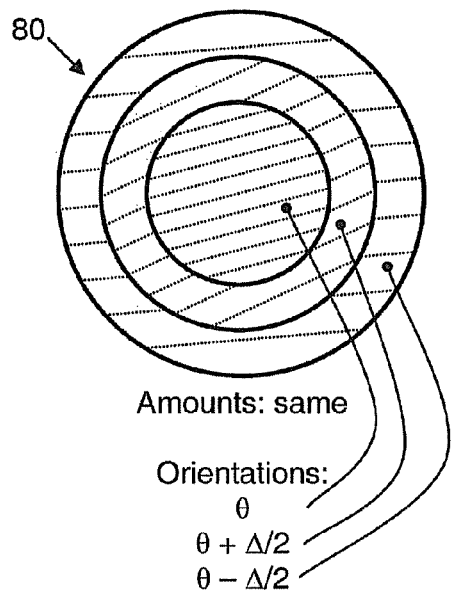
FIG. 8 is a schematic drawing of a pupil of an intraocular lens with three concentric zones.

In the pupil 80 of FIG. 8, there are three concentric zones, rather than two as in FIGS. 4, 6 and 7. The astigmatism amounts may be the same in all three zones. Alternatively, the astigmatism amounts may be the different in one or more zones, or different in all the zones. The astigmatism orientations may be different in all three zones, for example, with the orientation in one zone falling halfway between the orientations in the remaining two zones. In some embodiments, the orientation of the zones may be selected depending on the amount of astigmatism in each zone.

Figure 9:
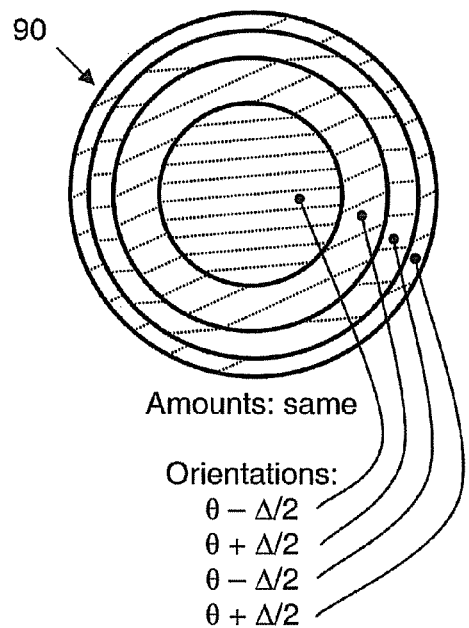
FIG. 9 is a schematic drawing of a pupil of an intraocular lens with four concentric zones, in which each zone has the same astigmatism amount and a different astigmatism orientation.

In the pupil 90 of FIG. 9, there are four concentric zones. The astigmatism amounts are the same in all four zones. The astigmatism orientations alternate between θ+Δ/2 and θ−Δ/2, when aligned to a cornea having an astigmatism orientation of θ.

Figure 10:
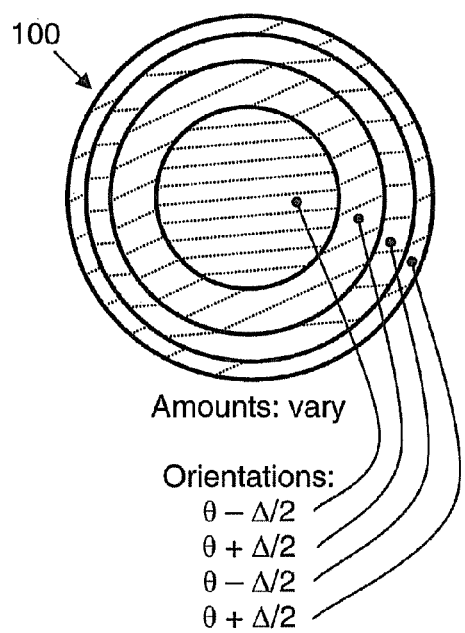
FIG. 10 is a schematic drawing of a pupil of an intraocular lens with four concentric zones, in which each zone has both a different astigmatism amount and a different astigmatism orientation.

In the pupil 100 of FIG. 10, the astigmatism amounts vary from zone-to-zone. The four zones may all have different astigmatism amounts, or at least one zone may have the same astigmatism amount as another zone.

Figure 11:
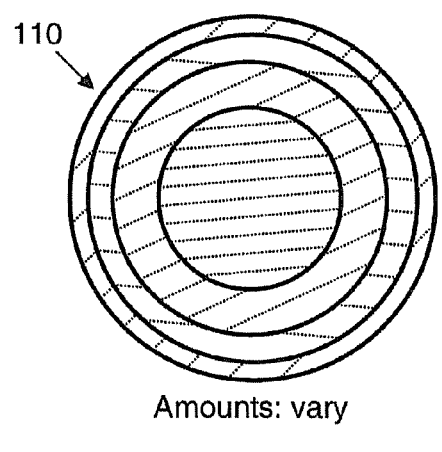
FIG. 11 is a schematic drawing of a pupil of an intraocular lens with four concentric zones, in which each zone has both a different astigmatism amount and a different astigmatism orientation.

In the pupil 110 of FIG. 11, both the astigmatism amounts and the astigmatism orientations may vary from zone-to-zone. The four zones may all have different astigmatism orientations, or at least one zone may have the same astigmatism orientation as another zone.

As a further alternative not shown in the figures, there may be additional concentric zones, numbering five, six, or any suitable value more than six. The astigmatism amounts and/or orientations may be the same in all the zones, may be different in at least two zones, or may be different in all the zones.

In addition to having purely concentric zones, the lens pupil may optionally have one or more of the concentric zones further divided into one or more azimuthal zones. For instance, the pupil 120 in FIG. 12 has a central zone, surrounded on one side by one azimuthal zone and on the opposite side by a second azimuthal zone. The zones may all have the same astigmatism amounts. The two azimuthal zones in pupil 120 have astigmatism orientations that differ from each other by angle Δ and differ from the central zone by Δ/2. Alternatively, the astigmatism orientations of the azimuthal zones may have any particular orientation with respect to the central zone and to each other. Note that in FIG. 12 the boundary between the azimuthal zones is aligned with the astigmatism orientation in the central zone. Alternatively, this boundary may be at an angle to the astigmatism orientation in the central zone.

Figure 12:
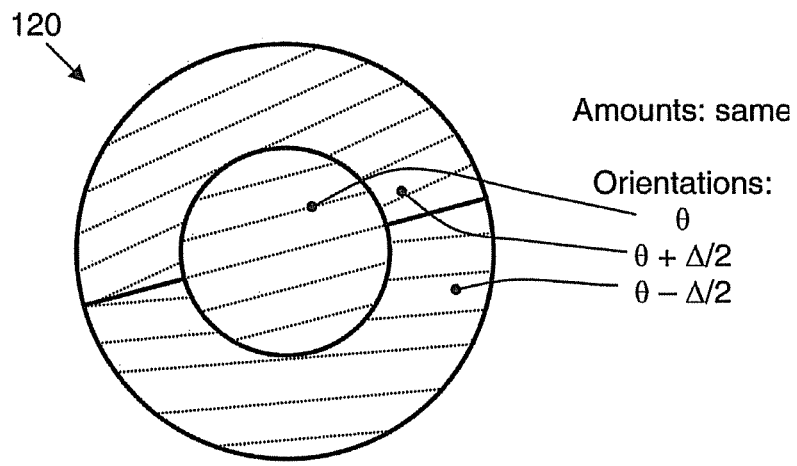
FIG. 12 is a schematic drawing of a pupil of an intraocular lens with two azimuthal zones.
Figure 13:
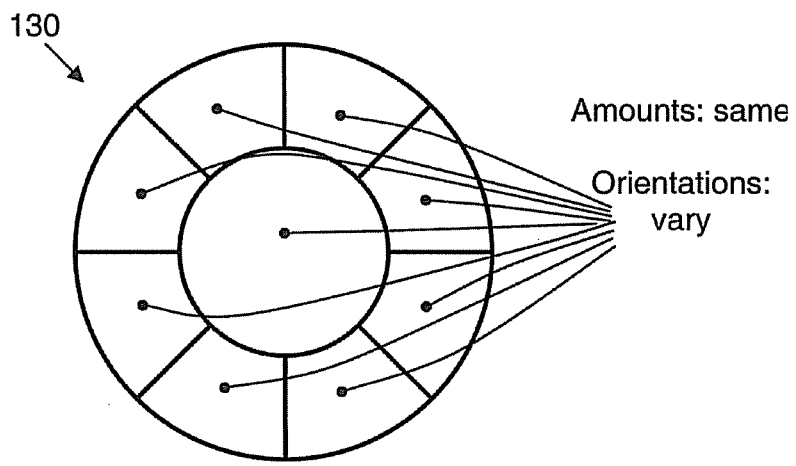
FIG. 13 is a schematic drawing of a pupil of an intraocular lens with eight azimuthal zones, in which each zone has the same astigmatism amount and a different astigmatism orientation.

In the pupil 130 of FIG. 13, there are eight azimuthal zones, rather than the two shown in pupil 120 of FIG. 12. The astigmatism amounts are the same in all the zones, and the astigmatism orientations may be different in one or more zones. Note that the azimuthal zones of pupil 130 all subtend the same azimuthal angle. Alternatively, one or more azimuthal zones may subtend a different azimuthal angle from any another azimuthal zone. Alternatively, there may be more or fewer than eight azimuthal zones.

Figure 14:
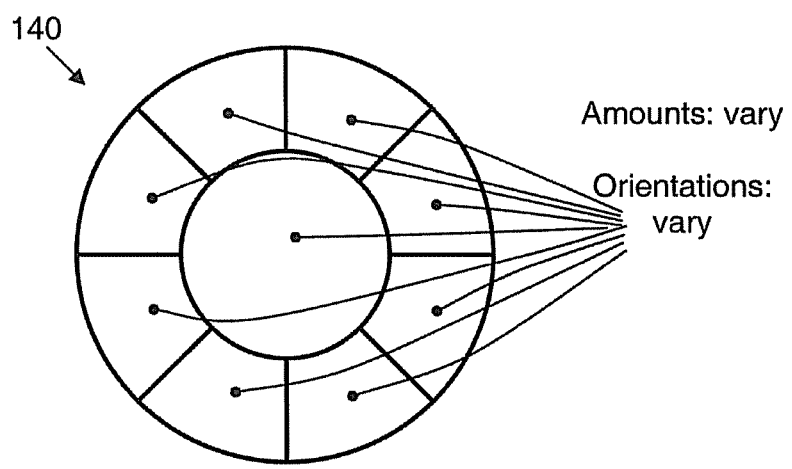
FIG. 14 is a schematic drawing of a pupil of an intraocular lens with eight azimuthal zones, in which each zone has both a different astigmatism amount and a different astigmatism orientation.

In the pupil 140 of FIG. 14, both the astigmatism amounts and the astigmatism orientations may differ from zone-to-zone.

Although the lenses in FIGS. 4 and 6-14 have circular, concentric zones, other zone shapes may be used as well. For instance, a particular zone may be elliptical, or elongated in a particular dimension. Or, a particular zone may be spiral-shaped, have a straight or curved edge, have one or more corners, or may be any other suitable shape.

The lens pupils shown schematically herein show only the spatial locations (x, y) of lens astigmatism amounts and orientations. The source of this lens astigmatism may be any combination of a toric or anamorphic anterior refractive surface, a toric or anamorphic posterior refractive surface, and a diffractive element made integral with or attached to the anterior surface and/or the posterior surface. The toric or anamorphic surfaces may have a cross-section that may be spherical in shape, or may optionally have aspheric terms and/or a non-zero conic constant.

In some embodiments, a lens comprises more zones than those illustrated in FIGS. 4-14. In other embodiments, portions of the lens or the entire lens may be configured so that the amount of astigmatism or the orientation of an astigmatism varies continuously between adjacent zone.

Modification of Standard Toric Lens

Figure 15:
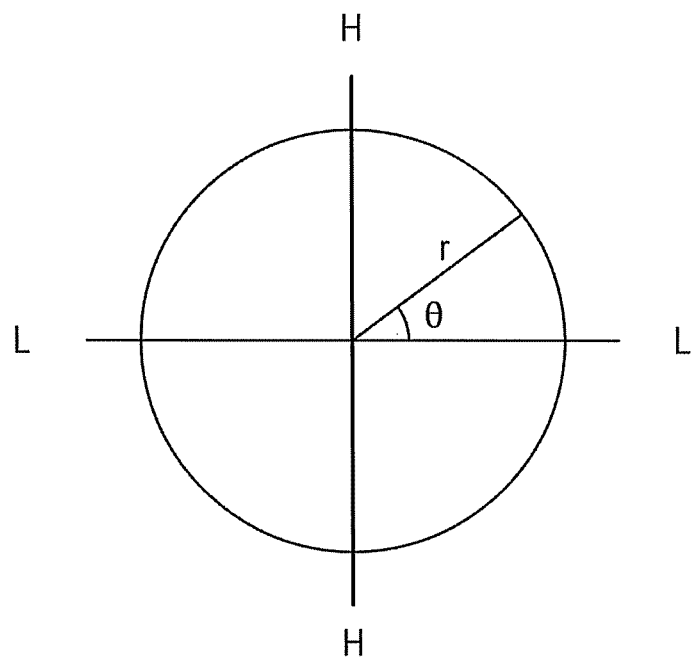
FIG. 15 is a diagram that represents power characteristics of a toric lens.

A toric ophthalmic lens may be characterized by a low amount of corrective power along an astigmatic axis and a high amount of corrective power along the axis that is orthogonal to its astigmatic axis. In this regard, FIG. 15 is a diagram that represents a coordinate system used for describing the power characteristics of a toric lens. In FIG. 15, the variable θ represents the meridian angle position relative to the astigmatic axis, and the variable r corresponds to the radial position along a given meridian. FIG. 15 includes labels ("H" and "L") that indicate the high and low power meridians. In accordance with well known and standard toric lens designs, the low power meridians correspond to angles of zero and 180 degrees, and the high power meridians correspond to angles of 90 and 270 degrees.

Figure 16:
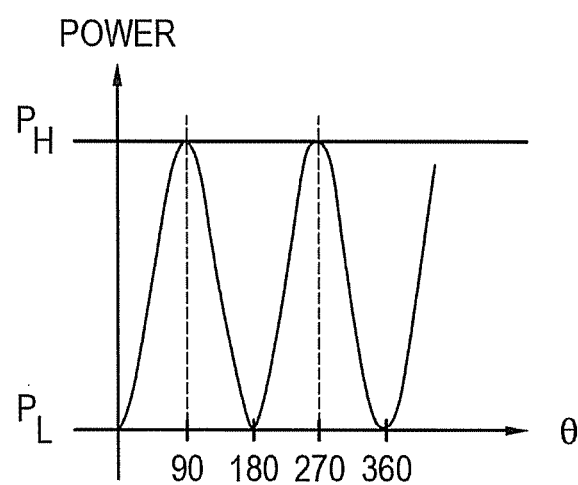
FIG. 16 is a graph that depicts power versus meridian angle position for a standard toric lens.
Figure 17:
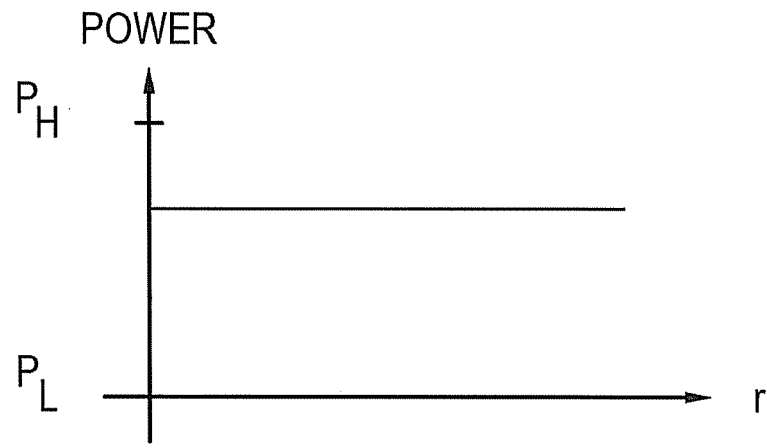
FIG. 17 is a graph that depicts power versus radial position for a standard toric lens.

A conventional and standard toric lens also has constant lens power along each meridian. However, the power varies with the meridian angle θ. Thus, each meridian in a standard toric lens corresponds to a respective constant power. More specifically, the power varies in accordance with a sine squared function of θ. In this regard, FIG. 16 is a graph that depicts power versus meridian angle position for a standard toric lens. As depicted in FIG. 16, the power of a standard toric lens will be at its low value at zero degrees, at its high value at 90 degrees, at its low value at 180 degrees, and at its high value at 270 degrees. Notably, the graph depicted in FIG. 16 applies to any value of r of a standard toric lens, so that the power will be constant (and between the high and low corrective power values, inclusive) along any given meridian. FIG. 17 depicts power versus radial position for a standard toric lens, along a given meridian (i.e., the angle θ is held constant). FIG. 17 shows that the power remains constant for a meridian, regardless of the radial dimension r.

The power characteristics of the toric lenses described in more detail below do not follow the traditional and standard toric functions. Instead, a toric lens function results in non-constant power along at least one meridian and/or a power that varies with meridian angle θ according to a function that is different from a sine squared function of θ. For example, one embodiment described below is characterized by a modification or modulation function that results in declining power (from the center to the periphery) along all meridians or along certain designated meridians, which can help to make the toric lens tolerant of rotational misalignment, which might result during implantation. For another embodiment described below, the power along all meridians or along certain designated meridians increases and decreases in a manner that may also make the toric lens tolerant of rotational misalignment. Yet another embodiment could vary the power along all meridians or along certain designated meridians in a customized manner that accommodates the particular needs of each patient. In still other embodiments, the power varies with the meridian angle θ according to a function that has a first derivative at the high and low power meridians that is smaller than the first derivative of the sine squared function of a traditional toric lens at the high and low power meridians.

The toric ophthalmic lens embodiments described below include optical elements having optical characteristics that are influenced by the relationship $P(r,\theta)=P_0(r,\theta)*Ap(r,\theta)$, wherein:

$P_0$=baseline toric lens function that defines constant power for each meridian (e.g., as depicted in FIGS. 16 and 17);
r=radial position;
θ=angular position relative to a reference meridian;
Ap=a modification function;

*=an adjustment or modification operator; and

P(r,θ) is the power defined at a particular meridian angle (θ) and a particular point or radial length (r) along the meridian.

A suitably designed modification function can be utilized in a method of manufacturing a toric ophthalmic lens as described here. As used herein, a "modification" function includes, without limitation, a function that results in the modulation, variation, apodization, customization, or alteration of lens power characteristics of a baseline lens. As a preliminary step in the manufacturing method, an appropriate toric lens function, such as the standard toric lens function $P_0$, may be provided. Then, the modification function is applied to the baseline toric lens function. In this regard, the modification function modifies the baseline toric lens function to obtain a modified toric lens function having the desired optical characteristics. The modified toric lens function can then be used to fabricate the toric ophthalmic lens, using known manufacturing techniques and technologies. In this regard, the optical characteristics and qualities of the resulting toric ophthalmic lens will be influenced by the modified toric lens function. In some embodiments, the lens may be manufactured according to the function P(r,θ), wherein the baseline and modification functions are convenient ways of characterizing the lens into component parts.

Although the following description assumes that $P_0$ represents a conventional standard toric lens function, the modification function could be selected to cooperate with, and modify, any toric or other lens function. The modification function is conceptually akin to a filter that enhances desired image characteristics and optical qualities, while removing unwanted image characteristics and optical qualities. Notably, the modification function may be a function of radial position, angular position, or both. In practice, the modification function may represent a customized function that is influenced by the measured characteristics of the patient. Alternatively, the modification function may be designed to accommodate the needs of a category or class of patients, for example, that fall within a designated prescription range and/or have a common condition (e.g., age, pupil size, axial length of the eye, natural lens power, presence of a cataract, prior refractive surgical procedure, etc.). Thus, a plurality of different modification functions could be used to manufacture a limited number of toric lenses to form a "kit" that accommodates common prescriptions for astigmatic patients. For a given toric lens, a suitable modification or modulating function can be selected such that the baseline toric function will be modified in a desired fashion, resulting in a non-standard toric lens function. In turn, a non-standard toric lens can be fabricated in accordance with the resulting non-standard toric lens function.

First Example

Figure 18:
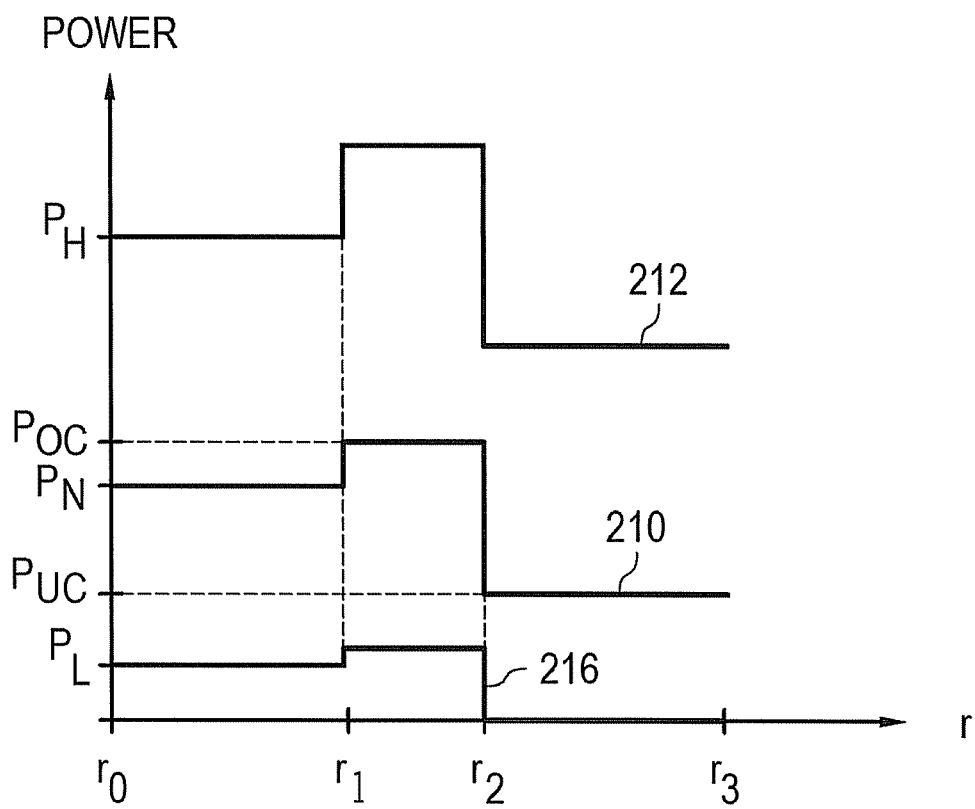
FIG. 18 is a graph that depicts power versus radial position for a first embodiment of a toric lens having radially variable characteristics.
Figure 19:
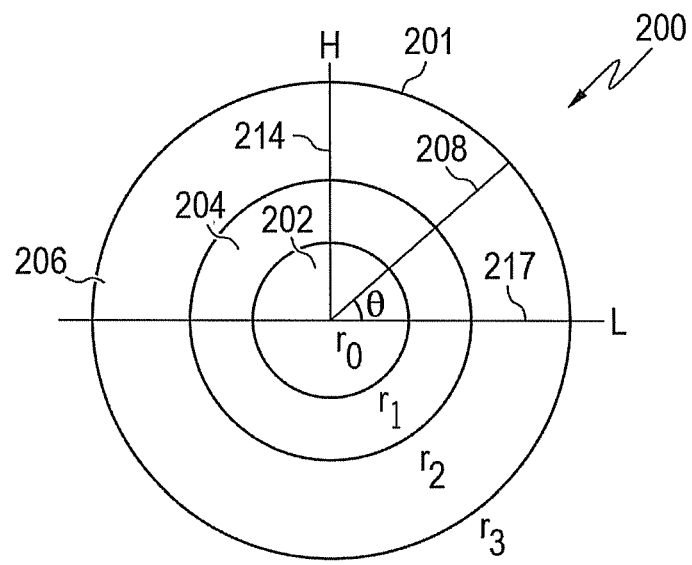
FIG. 19 is a schematic drawing of a pupil of a toric lens having the power characteristics depicted in FIG. 18.

FIG. 18 is a graph that depicts power versus radial position (along a meridian) for a first embodiment of a toric lens having radially modulated characteristics. FIG. 19 is a schematic drawing of an optical element or lens 200 having a clear aperture 201 and the power characteristics depicted in FIG. 18 (as used herein, the term "clear aperture" means the opening of a lens or optic that restricts the extent of a bundle of rays from a collimated source or a distant light source that can imaged or focused by the lens or optic). In FIG. 19, the horizontal axis represents the low power meridian (labeled "L") and the vertical axis represents the high power meridian (labeled "H"). For this example, $r_0$ is the originating position (which has a value of zero in the illustrated embodiment), $r_1$ is the radial position that defines a central zone 202, $r_2$ is the radial position that defines the outer boundary of an intermediate zone 204, and $r_3$ is the radial position that defines the outer boundary of an outer zone 206. Accordingly, the intermediate zone 204 represents the area defined by $r_1$ and $r_2$, and the outer zone 206 represents the area defined by $r_2$ and $r_3$. In certain embodiments, $r_1$ can be up to about 2.0 mm, $r_2$ is between $r_1$ and about 2.5 mm, and $r_3$ is between $r_2$ and about 3.5 mm. These ranges are merely indicative of some practical embodiments, and the actual dimensions and number of zones may differ from one lens to another. As used herein, the term "about" means within plus or minus 0.1 mm, when used in reference to a linear distance specified in millimeters.

In contrast to standard toric lenses (where the power is constant along any meridian), the power of the optical element 200 varies along one or more meridians, such as the depicted meridian 208. As depicted in FIG. 19, the meridian 208 corresponds to the angle θ, which is measured from the horizontal axis. For this particular embodiment, the power along the meridian 208 follows the plot 210 depicted in FIG. 18. Thus, the power along the meridian 208 is a constant nominal power within the central zone 202, is greater than the nominal power within the intermediate zone 204, and is less than the nominal power within the outer zone 206. In practice, the nominal value (labeled $P_N$ in FIG. 18) may correspond to the power of a conventional standard toric lens at the same meridian. In other words, the modification function for the optical element 200 may have little to no effect on the baseline toric function in the central zone 202. In the intermediate zone 204, however, the optical element 200 provides overcorrection power for the patient. This higher power is labeled $P_{OC}$ in FIG. 18. Conversely, in the outer zone 206, the optical element 200 provides undercorrection power for the patient. This lower power is labeled $P_{UC}$ in FIG. 18.

The power along the meridian 208 provides overcorrection and undercorrection, which can reduce or compensate for error due to rotational misalignment during implantation of the lens and/or due to movement of the lens subsequent to implantation. The central zone 202 retains the nominal power because the center of the lens is less sensitive to rotational misalignment. The intermediate zone 204, which is sized to accommodate pupil size in reasonably lit or mesopic conditions, provides overcorrection. Thus, if the lens is implanted with little to no rotational misalignment, then the overcorrection in the intermediate zone 204 under moderate or mesopic lighting conditions will result in slight myopia. However, slight myopia is tolerable because the patient will retain some range of vision where objects will appear in focus without the use of spectacles or contact lenses. If the lens is implanted with some rotational misalignment, the power of the intermediate zone 204 will still allow the patient to retain some range of vision, and may even slightly better vision than if the central zone were perfectly aligned. The outer zone 206 provides undercorrection because that zone will have an effect under low light or photopic conditions when the pupil is larger. Under such conditions, some of the overcorrecting effect of the intermediate zone 204 will be compensated by the undercorrecting effect of the outer zone 206. The amount of overcorrection and the amount of undercorrection can be selected to enhance an optical figure of merit for the lens or lens system provided when implanted with the eye of a patient, to decrease the sensitivity to rotational misalignment, or the like. For example, the amount of overcorrection will typically be (but is not limited to) no more than about 0.75 diopters higher than the nominal power, and the amount of undercorrection will typically be (but is not limited to) no less than about 0.75 diopters lower than the nominal power. In some embodiments, the astigmatic axis of one or more of zones 202, 204, 206 may be rotated relative to some absolute astigmatic axis (e.g., as illustrated in FIGS. 4, and 6-11). As used herein, the term "about" means within plus or minus 0.25 diopters, when used in reference to an optical power specified in diopters.

The power can vary along a meridian in a manner that makes the lens less sensitive to rotational misalignment. For example, referring to the plot 210 in FIG. 18, the average power along the meridian 208 may be selected to be equal to $P_N$ (or any desired value). Alternatively, the average power based on lens area may be selected to be equal to $P_N$ (or any desired power). In some embodiment, along a meridian (such as the high power meridian, for example), the integral of power times radius squared is equal to the nominal power times the radius squared of a clear aperture of the optical element. Consequently, the value of $P_{OC}$ and/or the value of $P_{UC}$ could be constrained by certain design parameters.

The values of $P_N$, $P_{OC}$, and $P_{UC}$ will typically vary from one meridian to another. For instance, as is the case with a traditional toric lens, the nominal value $P_N$ could vary between a high value $P_H$ and a low value $P_L$. In this regard, the plot 212 in FIG. 18 represents an exemplary power characteristic along the high meridian 214 (FIG. 19). For the plot 212, the nominal value (labeled $P_H$ in FIG. 18) could correspond to the maximum power of a conventional standard toric lens along its high power meridians, as appropriate for the patient. The values of $P_{OC}$ and $P_{UC}$ associated with the plot 212 are higher than their counterparts in plot 210.

FIG. 18 also includes a plot 216 corresponding to yet the low power meridian 217 of the optical element 200. The amount of overcorrection and under correction in the plot 216 is noticeably less in absolute power difference than that defined by the plot 210 or the plot 212. This illustrates how the amount of overcorrection (or undercorrection) may vary from one meridian to another. In some embodiments, the power along the low power meridian 217, or one or more other meridians, is constant or substantially constant. In some embodiments, the power $P_{OC}$ and $P_{UC}$ along each meridian of the optical element 200 is a constant amount above and below the nominal power $P_N$ for that meridian. Alternatively, the power $P_{OC}$ and $P_{UC}$ along each meridian of the optical element 200 is a fixed percentage above and below the nominal power $P_N$ for that meridian. In yet other embodiments, the power $P_{OC}$ and $P_{UC}$ along each meridian of the optical element 200 is a fixed percentage above and below the nominal power $P_N$ for that meridian minus a constant, for example, where the constant is the nominal power $P_N$ along the low power low meridian 217. In still other embodiment, the power along a plurality of meridians between a lower angle $\theta_L$ and an upper angle $\theta_U$ varies in an absolute or relative sense as described in this paragraph.

The radial modulation described above may be applied to all meridians of the optical element, or to only some of the meridians. Moreover, all of the meridians of a toric lens need not follow the same modification scheme. In other words, a single toric lens may be fabricated in accordance with a plurality of different modification functions, each modification function being applied to a different group or subset of meridians. In this regard, different zones (radially defined and/or angularly defined) may be governed by different modification functions. For instance, although FIG. 18 and FIG. 19 illustrate an embodiment having three radially defined zones, an embodiment may have more or less than three zones. Moreover, the manner in which the power varies along a meridian may differ from that depicted in FIG. 18, which represents only one possible implementation. For example, the power along a meridian may vary between an upper overcorrection value and a lower undercorrection value, crossing the nominal value any number of times. As another example, the power along a meridian may vary between an upper overcorrection value and the nominal value, with any number of excursions above the nominal value. As yet another example, the power along a meridian may vary between a lower undercorrection value and the nominal value, with any number of excursions below the nominal value.

It should be appreciated that radial modulation as described here may be applied to a toric ophthalmic lens having zones with different toric orientations (as described above with reference to FIGS. 4-14). In this regard, one or more radial modification schemes may be applied to any of the different types of zones described previously.

Second Example

Figure 20:
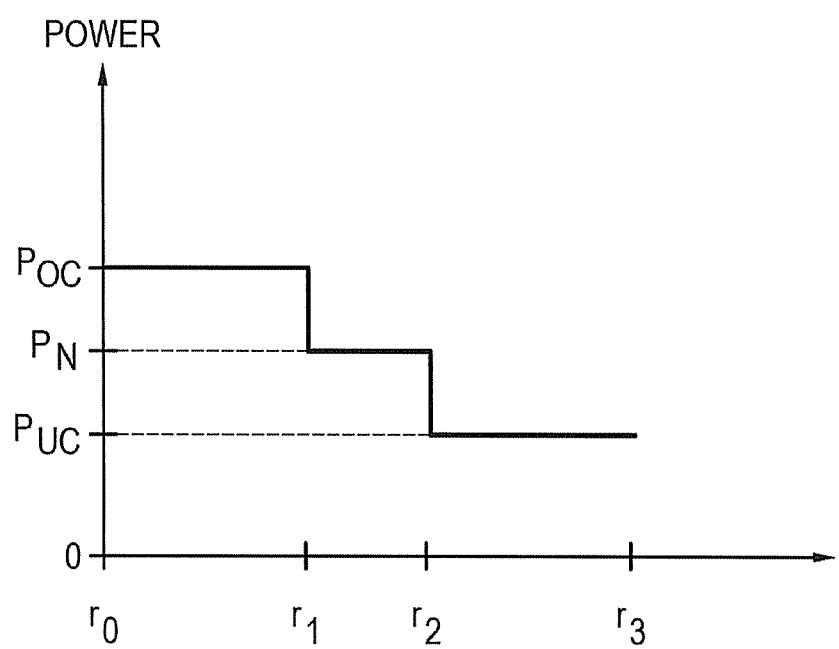
FIG. 20 is a graph that depicts power versus radial position for a second embodiment of a toric lens having radially modified characteristics.

The plots in FIG. 18 define the nominal power $P_N$ in the central zone 202, the overcorrecting power $P_{OC}$ in the intermediate zone 204, and the undercorrecting power $P_{UC}$ in the outer zone 206. In contrast, FIG. 20 is a graph that depicts power versus radial position (along one meridian) for a different embodiment of a radially modified toric lens. Here, the central zone (between $r_0$ and $r_1$) has an overcorrecting lens power, the intermediate zone (between $r_1$ and $r_2$) has the nominal lens power, and the outer zone (between $r_2$ and $r_3$) has an undercorrecting lens power. As mentioned above with reference to FIG. 18, the general characteristic of the plot in FIG. 20 may be followed by some or all of the meridians of the optical element. Moreover, the values of $P_{OC}$, $P_N$, and $P_{UC}$ may vary with the meridian angle $\theta$ according to any of the embodiments described above in relation to FIGS. 18 and 19. For example, the power along the low power meridian 217, or one or more other meridians, may constant or substantially constant. Additionally or alternatively, the variation of $P_{OC}$ and $P_{UC}$ may vary in absolute or relative terms between any or all the meridians according to any of the embodiments described above in relation to FIG. 18. $P_N$ might be at its lowest value at zero degrees, and at its highest value at 90 degrees. In some embodiments, the power $P_{OC}$ in FIG. 20 along a high power axis of the optical element corresponds to the astigmatic power of a conventional toric lens. Alternatively, the nominal power $P_N$ in FIG. 20 along a high power axis of the optical element corresponds to the astigmatic power of a conventional toric lens.

Third Example

Figure 21:
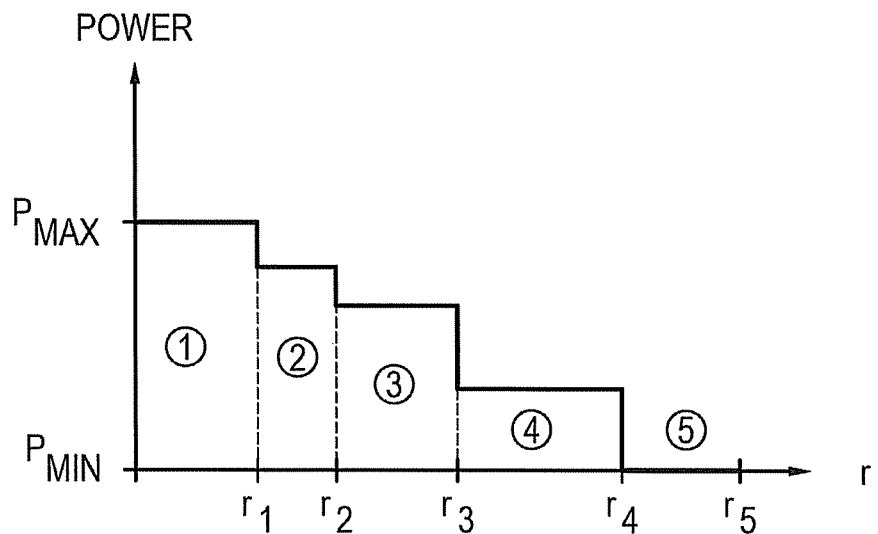
FIG. 21 is a graph that depicts power versus radial position for a third embodiment of a toric lens having radially variable characteristics.

FIG. 21 is a graph that depicts power versus radius for a toric lens, where the power monotonically decreases in a stepwise manner. The power characteristic depicted in FIG. 21 may be realized using a toric lens having five annular zones that are defined by the five radii (labeled $r_1$ to $r_5$ in FIG. 21). In practice, the number of steps and the height of each step will be chosen to best suit the needs of the given patient or class of patient. In certain embodiments, the power along one or more meridians may decrease in a continuous manner in one zone and decrease in stepwise manner in another zone. In other words, the modification scheme may result in a "hybrid" approach that combines continuous and stepwise transitions along a given meridian. The values of $P_{OC}$, $P_N$, and $P_{UC}$ may vary with the meridian angle $\theta$ in an absolute or relative sense according to any of the embodiments described above in relation to FIGS. 18 and 19. In some embodiments, the power $P_{OC}$ in FIG. 21 along a high power axis of the optical element corresponds to the astigmatic power of a conventional toric lens. Alternatively, the nominal power $P_N$ in FIG. 21 along a high power axis of the optical element corresponds to the astigmatic power of a conventional toric lens.

Fourth Example

Figure 22:
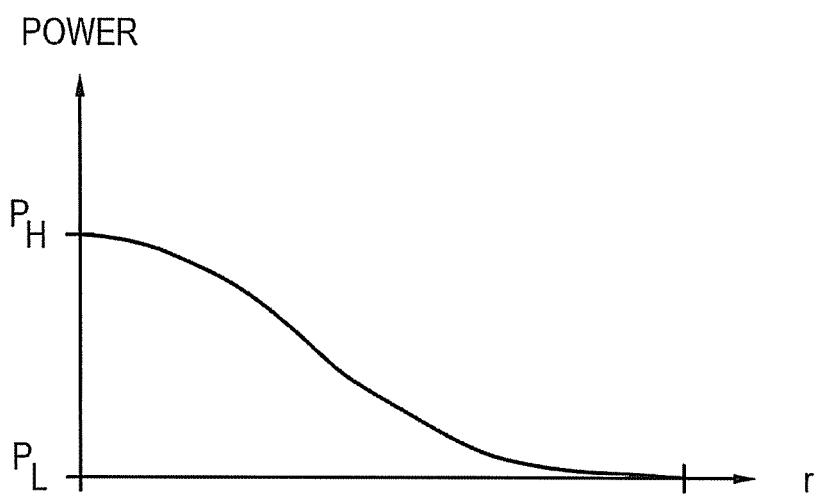
FIG. 22 is a graph that depicts power versus radial position for a fourth embodiment of a toric lens having radially variable characteristics.

FIG. 22 is a graph that depicts power versus radial position (along one meridian) for another embodiment of a toric lens having radially modified characteristics. For this example, the power monotonically decreases with increasing radial position from a maximum value $P_{Max}$ to a minimum value $P_{Min}$. Although not always required, this particular embodiment monotonically decreases to $P_{Min}$. It should be appreciated that "monotonically" is used here in the traditional mathematical sense. Thus, the slope of the graph shown in FIG. 22 is either negative (sloping downward) or zero (flat) at any point. In certain embodiments, the toric lens may be monotonically and strictly decreasing, i.e., the slope of the graph is always negative and nonzero. The values of $P_{Max}$ and $P_{Min}$ may vary with the meridian angle θ in an absolute or relative sense according to any of the embodiments described above in relation to FIGS. 18 and 19. In some embodiments, the power $P_{Max}$ in FIG. 21 along a high power axis of the optical element corresponds to the astigmatic power of a conventional toric lens.

The value of the maximum power for any or all meridians may depend upon the characteristics of the patient's cornea. In some instances, the maximum power corresponds to the power of a conventional and standard toric lens at that meridian. In other words, the modification function has no impact when r=0. FIG. 22 corresponds to an embodiment where the power gradually decreases in a monotonic manner until it reaches a minimum value at a radial position that is inside the outer periphery of the optical element.

The graph of FIG. 22 monotonically decreases in a smooth and continuous manner. Although a continuous decrease in power may be desirable in some circumstances, it is not a requirement. In this regard, FIG. 21 depicts an embodiment having a monotonically decreasing stepwise function.

The monotonically decreasing radial modification described above may be applied to all meridians of the toric lens, or to only some of the meridians. Moreover, the meridians of a toric lens need not follow the same modification scheme, and the manner in which the power varies along a meridian may differ from that depicted in FIG. 21 and FIG. 22. It should also be appreciated that monotonically decreasing radial modification as described here may be applied to a toric ophthalmic lens having zones with different toric orientations (as described above with reference to FIGS. 4-14). In this regard, one or more radial modification schemes may be applied to any of the different types of zones described previously.

The toric lens embodiments represented by FIGS. 20 and 21 have monotonically decreasing power with radius along a meridian. Other embodiments could employ monotonically increasing power with radius along a meridian (continuous, stepwise, or a combination thereof). Thus, a suitable modification function for a toric ophthalmic lens could result in monotonically varying power with radius, and the variation could be decreasing or increasing depending upon the embodiment.

Fifth Example

Figure 23:
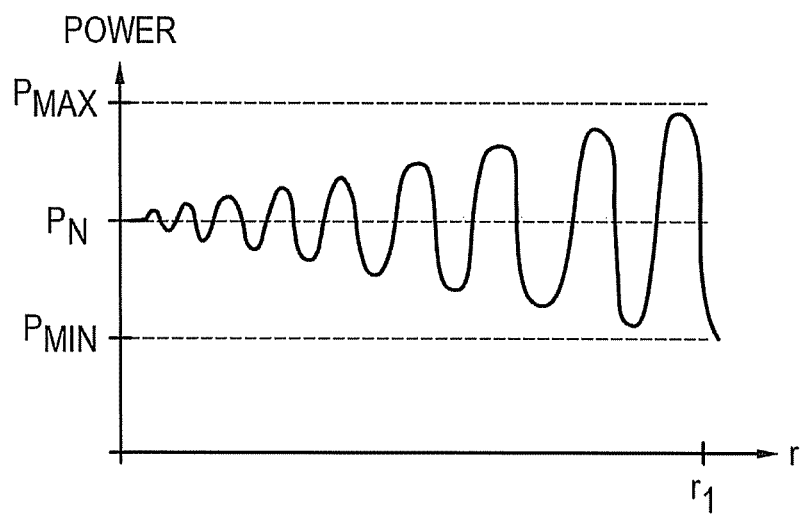
FIG. 23 is a graph that depicts power versus radial position for a fifth embodiment of a toric lens having radially variable characteristics.

FIG. 23 is a graph that depicts power versus radial position (along one meridian) for yet another embodiment of a toric lens having radially modulated characteristics. For this example, the power fluctuates relative to a nominal power (labeled $P_N$), with oscillations that increase in amplitude for increasing radius. When along the axis perpendicular to the astigmatic axis of the optical element, this nominal value $P_N$ may correspond to the maximum power of a conventional standard toric lens along its high power meridians, and as suitable for the patient. In other words, absent the modification function, the graph of FIG. 23 would be a horizontal line corresponding to a constant value of $P_N$ along a high power meridian of the lens. As with the other embodiments described herein, the specific value of $P_N$ generally varies from one meridian of the optical element to another.

For the example depicted in FIG. 23, the power along the meridian is generally bounded by an imaginary cone-shaped envelope. This envelope may be defined in any predetermined manner and by any suitable function or relationship. The upper boundary of the envelope in the illustrated example is defined by the value of $P_N$ at r=0, and by a maximum power value (labeled "$P_{Max}$") at a reference radius (labeled $r_1$). Similarly, the lower boundary of the envelope in the illustrated example is defined by the value of $P_N$ at r=0, and by a minimum power value (labeled "$P_{Min}$") at $r_1$. For a monofocal lens, the low and high values may typically be (without limitation) about 0.75 diopters above and below $P_N$.

The radially modified power varies between the upper and lower boundaries of this envelope, while crossing the $P_N$ value numerous times (the number of "cycles" or undulations may vary from one lens to another, and may vary from one meridian of the lens to another meridian of the same lens). For this embodiment, the power is $P_N$ at r=0, and the power eventually reaches the low value $P_{Min}$ at r=$r_1$. The number of times that the graph crosses the $P_N$ value can vary from one embodiment to another. Moreover, although FIG. 23 depicts a smooth and continuous function, a radially modified toric lens could be manufactured using a similar function that includes discrete steps (as described above with reference to FIG. 18 and FIG. 21).

Although FIG. 23 illustrates a generally cone-shaped envelope with straight edges, the actual boundary of the modified power function need not be shaped in this manner. Indeed, the envelope may be defined by any suitable function, which may be based upon, for example, a polynomial function (e.g., quadratic function), a cosine relationship, a sine relationship, an exponential relationship, or the like. Moreover, the contour of the envelope may be characterized by an increasing trend as depicted in FIG. 23, a decreasing trend, or it might have a fluctuating characteristic. Furthermore, the envelope may increase or decrease in a monotonic or non-monotonic manner, depending upon the desired characteristics.

Notably, a toric lens could be radially modulated in a manner akin to that depicted in FIG. 23, but converging to the $P_N$ value, instead of the high and low power values $P_{Min}$ and $P_{Max}$, with increasing radial position. For such an embodiment, the power would be generally bounded by the low and high values $P_{Min}$ and $P_{Max}$ near the optical axis at r=0. Then, at r=$r_1$ the power would settle to the $P_N$ value.

The radially modified characteristic shown in FIG. 23 may be applied to all meridians of the optical element, or to only some of the meridians. Moreover, the meridians of a toric lens need not follow the same modification scheme, and the manner in which the power varies along a meridian may differ from that depicted in FIG. 23. It should also be appreciated that the modification scheme depicted in FIG. 23 could be applied to a toric ophthalmic lens having zones with different toric orientations (as described above with reference to FIGS. 4-14).

Sixth Example

As described above with reference to FIGS. 15-17, the traditional and standard toric lens function is based on a sine squared function of meridian angle θ and constant power with radius r along each meridian. In accordance with certain embodiments, however, the standard toric function is subjected to a suitable modification function that results in a modified toric function that deviates from the traditional sine squared relationship. A lens or optical element according to this embodiment is associated with an angular modification of the standard toric function, which may by in place of, or in addition to, the radial variation illustrated in previous embodiments of the present invention. Accordingly, for a constant radius, the power of a toric lens of this example still varies with θ (see FIG. 15), but in a manner that differs from that of a standard toric lens.

Figure 24:
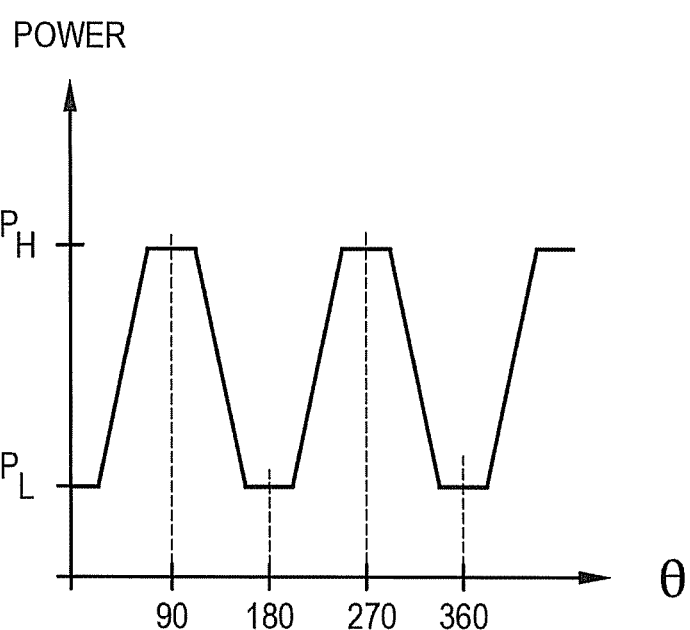
FIG. 24 is a graph that depicts power versus meridian angle position for an embodiment of a toric lens having angle variable characteristics.

In this regard, FIG. 24 is a graph that depicts power versus meridian angle position for an embodiment of a toric lens having angle modified/modulated characteristics. In accordance with one exemplary embodiment, the angle modified toric function resembles the standard sine squared toric function (see FIG. 16), but with its peaks and valleys truncated. This modified version of the standard toric lens function is defined between an upper (relatively high) power and a lower (relatively low) power, as labeled "$P_H$" and "$P_L$" in FIG. 23. The truncated characteristics of this modified function make the resulting toric lens less sensitive to rotational misalignment. In certain embodiments, the modified toric function illustrated in FIG. 24 is characterized by an angular or circumferential power that is constant near the astigmatic axis and the axis perpendicular to the astigmatic axis. Additionally or alternatively, the modified toric function may be characterized by a derivative of angular or circumferential power near the astigmatic axis (and/or the axis perpendicular thereto) that is less than the derivative of a sine squared function having the same astigmatic axis orientation and the same powers $P_L$ and $P_H$ at astigmatic axis and the axis perpendicular to the astigmatic axis, respectively. Additionally or alternatively, the modified toric function may be characterized by a derivative of angular or circumferential power that is greater than the derivative of the sine squared function at or near meridians located at angles of 45, 135, 225, 315 degrees from the astigmatic axis.

In practice, the standard toric lens function could be subjected to a modification function that performs both radial modification and angle modification. In other words, an embodiment of a toric lens may combine the different modification schemes described above.

Diffractive Implementation

A toric lens as described here may be realized using refractive and/or diffractive techniques. In this regard, a toric lens surface may include diffractive elements that are suitably configured in a manner that implements the desired modification scheme (radial and/or angular). In certain embodiments, the toric lens includes a suitably arranged diffraction grating that provides a first focus point and a second focus point. Diffractive elements or echelettes are well known to those familiar with ophthalmic lenses, and such diffractive elements will not be described in detail here.

In accordance with one preferred implementation, diffractive elements are utilized to create a toric lens having monotonically decreasing power along its meridians (e.g., see FIG. 21, FIG. 22, and accompanying description above). In this regard, the step height of the diffractive elements may monotonically decrease with increasing radius. In other words, the height of the diffractive elements may be at a maximum at the center of the lens and at a minimum at or near the outer periphery. In accordance with other embodiments, a toric lens may have refractive features that provide radially modified power characteristics as described herein. The base structure of the toric lens can therefore be designed to be less sensitive to rotational misalignment, and diffractive elements can be created on the base structure as desired.

Regarding the formation of diffractive elements on a toric lens, the techniques described in Baude et al., U.S. Pat. No. 5,016,977 and/or the techniques described in Lee et al., U.S. Pat. No. 5,699,142 could be utilized, all these references being herein incorporated by reference in their entirety.

Implementation Variations

As mentioned in the preceding section, a modified or modulated toric lens as described herein may be realized using refractive elements, diffractive elements, or a combination of both refractive and diffractive elements. One or more refractive or diffractive elements may be formed on one or both major surfaces of the modified toric lens, as appropriate for the particular embodiment. A modified toric IOL having the characteristics described herein can be manufactured using known techniques such that the desired refractive and/or diffractive elements are present on the surface or surfaces of the IOL prior to implantation. Alternatively, the modified cylinder structure could be fabricated onto a surface of the lens after implantation surgery, using, for example, light-adjustment techniques. Moreover, an appropriately engineered modified cylinder structure could be applied to the surface of the patient's cornea using, for example, laser-assisted surgical techniques.

Although the figures depict optical elements having a centered structure, the modified cylinder structure could be positioned eccentrically onto the optic surface. In other words, meridians of a modified toric lens might originate at point other than the center of the optical element, e.g., at a point that is offset relative to the true center of the optical element. Furthermore, although certain examples described herein utilize a horizontal line (zero degrees) as the reference astigmatic axis for the toric lens, the angle θ may actually be measured using any convenient reference axis.

For purposes of illustration, embodiments of the present invention have been directed to intraocular lenses; however, other types of lenses and ophthalmic lenses are anticipated. For example, embodiments of the present invention may be incorporated into contact lenses, corneal inlays, spectacles, or any suitable ophthalmic lens. In addition, embodiments of the present invention may be incorporated various types of ophthalmic lenses, for example, single-focus (monofocal) lenses, refractive lenses, diffractive lenses, dual-focus or bifocal lenses (refractive and/or diffractive), multifocal lenses (refractive and/or diffractive), or accommodating lenses move or change shape in order to provide varying amounts of diopter power.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A toric ophthalmic lens comprising an optic, the optic comprised of an anterior surface and a posterior surface with toric features on either the posterior or anterior surface, the toric features comprised of meridians, including a high power meridian and a low power meridian orthogonal to the high power meridian, with at least one radially modulated meridian along which power monotonically varies in a stepwise manner with increasing radial position.

2. The toric ophthalmic lens of claim 1, wherein the power along the at least one radially modulated meridian monotonically decreases with increasing radial position.

3. The toric ophthalmic lens of claim 1, wherein the power along the at least one radially modulated meridian monotonically increases with increasing radial position.

4. The toric ophthalmic lens of claim 1, wherein the power along the at least one radially modulated meridian monotonically decreases, with increasing radial position, to zero.

5. The toric ophthalmic lens of claim 4, wherein the power along the at least one radially modulated meridian reaches zero at a radial position inside a periphery of the optical element.

6. The toric ophthalmic lens of claim 1, further comprising a diffraction grating, wherein the diffraction grating provides a first focus point and a second focus point.

7. The toric ophthalmic lens of claim 1, wherein along the high power meridian, the integral of power times radius squared is equal to the nominal power times the area of a clear aperture of the optical element.

8. A toric ophthalmic lens comprising an optic, the optic comprised of an anterior surface and a posterior surface with toric features on either the posterior or anterior surface, the toric features having meridians associated therewith, including a high power meridian and a low power meridian orthogonal to the high power meridian, wherein along the high power meridian:
between an originating position and a respective first radial position, power equals a respective nominal power;
between the respective first radial position and a respective second radial position, power is greater than the respective nominal power; and
between the respective second radial position and a respective third radial position, power is less than the respective nominal power;
wherein the power between the originating position and the respective third radial position monotonically varies in a stepwise manner.

9. The toric ophthalmic lens of claim 8, wherein between the respective first radial position and the respective second radial position, the power equals an overcorrection power.

10. The toric ophthalmic lens of claim 9, wherein the overcorrection power exceeds the nominal power by no more than 1.5 diopters.

11. The toric ophthalmic lens of claim 8, wherein between the respective second radial position and the respective third radial position, the power equals an undercorrection power.

12. The toric ophthalmic lens of claim 11, wherein the nominal power exceeds the undercorrection power by no more than 1.5 diopters.

13. The toric ophthalmic lens of claim 8, wherein along the high power meridian, the integral of power times radius squared is equal to the nominal power times the area of a clear aperture of the optical element.

14. The toric ophthalmic lens of claim 8, wherein the optical element comprises a diffraction grating.

15. A method of manufacturing a toric ophthalmic lens having meridians associated therewith, including a reference meridian, a high power meridian, and a low power meridian orthogonal to the high power meridian, the method comprising:
providing a standard toric lens function that defines power such that each meridian corresponds to a respective constant power;
applying a modification function to the standard toric lens function to obtain a modified toric lens function, wherein the modification function is a function of radial position and angle position relative to the reference meridian, and wherein the modified toric lens function results in non-constant power along at least one meridian; wherein the non-constant power monotonically varies in a stepwise manner with increasing radial position; and
fabricating the toric ophthalmic lens in accordance with the modified toric lens function.

16. The method of claim 15, wherein the power along the at least one radially modified meridian monotonically decreases with increasing radial position.

17. The method of claim 15, wherein the power along the at least one radially modified meridian monotonically increases with increasing radial position.

18. The method of claim 15, wherein the modified toric lens function results in radially modified meridians along which power varies with increasing radial position, and for each radially modified meridian:
between an originating position and a respective first radial position, the power equals a respective nominal power;
between the respective first radial position and a respective second radial position, the power is greater than the respective nominal power; and
between the respective second radial position and a respective third radial position, the power is less than the respective nominal power.

19. The method of claim 18, wherein:
between the respective first radial position and the respective second radial position, the power equals an overcorrection power; and
between the respective second radial position and the respective third radial position, the power equals an undercorrection power.

20. The method of claim 15, wherein fabricating the toric ophthalmic lens comprises the step of creating a diffraction grating.

* * * * *